(12) United States Patent
Teng et al.

(10) Patent No.: US 8,673,864 B2
(45) Date of Patent: Mar. 18, 2014

(54) MANGIFERIN-BERBERINE SALT, MANUFACTURING METHOD AND USE THEREOF

(75) Inventors: Houlei Teng, Haikou (CN); Wei Wu, Haikou (CN)

(73) Assignee: Hainan Deze Drug Research Co., Ltd., Haikou, Hainan (CN)

( * ) Notice: Subject to any disclaimer, the term of this patent is extended or adjusted under 35 U.S.C. 154(b) by 152 days.

(21) Appl. No.: 13/377,863

(22) PCT Filed: Jun. 3, 2010

(86) PCT No.: PCT/CN2010/000791
§ 371 (c)(1),
(2), (4) Date: Dec. 13, 2011

(87) PCT Pub. No.: WO2010/145192
PCT Pub. Date: Dec. 23, 2010

(65) Prior Publication Data
US 2012/0094941 A1    Apr. 19, 2012

(30) Foreign Application Priority Data

Jun. 16, 2009   (CN) .......................... 2009 1 0040336

(51) Int. Cl.
*A61K 31/70* (2006.01)
*C07H 1/00* (2006.01)
*C07H 15/04* (2006.01)

(52) U.S. Cl.
USPC ............. 514/23; 536/1.11; 536/120; 536/124

(58) Field of Classification Search
None
See application file for complete search history.

(56) References Cited

U.S. PATENT DOCUMENTS 7,867,979 B2 *  1/2011  Xu .................................. 514/23

* cited by examiner

*Primary Examiner* — Traviss C McIntosh, III
(74) *Attorney, Agent, or Firm* — Morris Manning & Martin LLP; Tim Tingkang Xia, Esq.

(57) ABSTRACT

The present invention provides a mangiferin-berberine salt and manufacturing method thereof. Otherwise, the present invention also provides the use of mangiferin-berberine salt as AMPK activator.

8 Claims, 6 Drawing Sheets

MANGIFERIN-BERBERINE SALT, MANUFACTURING METHOD AND USE THEREOF

FIELD OF INVENTION

The present invention relates to a mangiferin-berberine salt and its preparation method and use as an AMPK activator.

BACKGROUND

Mangiferin is a natural polyphenol with structural formula: $C_{19}H_{18}O_{11}$, molecular weight: 422, and its chemical structure is as follows:

Berberine is isoquinoline alkaloid. Molecular formula: $[C_{20}H_{18}NO_4]^+$, molecular weight: 336.37 and its chemical structure is as follows:

Li'Xuejian group of GuangXi Traditional Chinese Medical University published patent specification 【Publication Number: CN101066275A; Title: mangiferin-berberine composition】, the first paragraph in summary of the invention discusses: "mangiferin is acidic, and berberine (or its salt) is alkaline; under certain conditions, they can react to produced mangiferin-berberine composition. It is defined as composition, because the combination is not very strong, only the acting result of van der Waals forces between molecules. This composition at large concentration, or when is digested in the body, is separated and of independent existence with each other, which create the conditions for playing their respective pharmacological effects. The fifth paragraph discusses: the results show that the mangiferin-berberine composition solution is very stable, If the concentration of it is less than 2.5%, even if it is stored in 5° C. environment, it can not precipitate crystals; If the concentration of it is from 2.5% to 5%, it can not precipitate crystals in eight hours after confected; If the concentration of it is from 5% to 10%, it can not precipitate crystals in three hours after confected".

Analyze the technology project as above, we can know: first, the chemical substance that it describes is "the composition under state of solution"; secondly, because the chemical substance is the composition under state of solution, so there are the following defects:

1. The stability of the mangiferin-berberine composition is bad. According to public content of the patent specification, the composition can maintain stability for several hours; but a drug must maintain stability for more than one year, so that the stability of the mangiferin-berberine composition is bad in the technical project as above.

2. The mangiferin-berberine composition is not stored easily.

3. The mangiferin-berberine composition can not be prepared to solid formulations. The patent specification only disclosed the liquid or semi-solid formulations that the composition was prepared; there is no content of solid formulation.

The composition that is composed of mangiferin and berberine, that we disclosed 【Publication Number: WO/2008/043246; Title: DRUG COMPOSITION FOR TREATING 2 TYPE DIABETES AND ITS CHRONICITY NEOPATHY】 is only the composition that mangiferin and berberine mix by certain ratio, did not involve the reaction or bonding material between two compounds.

CN101066275A disclosed the method for the composition under state of solution, although mangiferin is acidic, and berberine (or its salt) is alkaline, under the reaction conditions that it disclosed, mangiferin-berberine salt can not be gotten. The specification discusses that mangiferin is acidic, and berberine (or its salt) is alkaline, under certain conditions, they can react to produce mangiferin-berberine composition. It is defined as composition, because the combination is not very strong, only the acting results of van der Waals forces between molecules.

In summary, the technology enlightenment that mangiferin and berberine bonding material to form mangiferin-berberine salt by reaction is not gained from the above open references.

Adenosine monophosphate (AMP)-activated protein kinase (AMPK) is a protein kinase that regulates energy metabolism in a cell. With the research about AMPK gradually develops, in metabolic diseases, cardiovascular diseases, neurological diseases, inflammatory diseases, cancer, muscular system diseases, AMPK play a crucial role; AMPK is becoming a new target for disease treatment, but there is not yet the AMPK activator in the market; the research and development of AMPK activators have important clinical significance 【Li ji. AMPK: A new treatment target of diabetes and cardiovascular disease. China Medical Tribune, 2009, (1149); Ren jun-fang. AMPK and cardiovascular remodeling. Journal of International Pathology and Clinical Medicine, 2008, 28(1): 33-36; Ricardo Lage, Carlos Dieguez, Antonio Vidal-Puig. et al. AMPK: a metabolic gauge regulating whole-body energy homeostasis. Trends Mol Med, 2008, 14(12): 539-49; Fu Qing-Ying, Gao Yu-Qi. Advances in the studies of AMP-activated protein kinase. Chinese Bulletin of Life Sciences, 17(2): 147-152; CHEN Qi, Liang Hou-jie, Zou Lan, et al. Expression of cyclooxygenase-2 by the activation of adenosine monophosphate protein kinase and the relationship between the expression and chemosensitivity of 5-Fluorour-acil in colon cancer. Practical Journal of Clinical Medicine, 2008, 5(3): 56-58 and so on】.

SUMMARY OF INVENTION

We get creatively derive mangiferin-berberine salt based on a lot of research. The chemical substance of mangiferin-berberine salt is compound that the mangiferin-berberine salt are linked by ionic bonding material; it has the following characteristics, compared to mangiferin-berberine composition [CN101066275A]:
1. The stability of the mangiferin-berberine salt is good.
2. The mangiferin-berberine salt may be prepared to solid, liquid and other all kinds of formulations.
3. The mangiferin-berberine salt is stored easily.

In addition, the mangiferin-berberine salt has shown the following unexpected technical effect:

Our study found that mangiferin-berberine salt dissolves in strong acid solution; the smaller the pH is, the better it dissolves. In the acid solution that the pH is 1-3, the concentration of mangiferin-berberine salt solution is below 2 mg/ml; within 12 hours precipitation is only traces; when the concentration of mangiferin-berberine salt solution is greater than 4 mg/ml, the it precipitates soon after it dissolves. As the pH of human gastric juice is 1-3, the above properties of mangiferin-berberine salt can be well dissolved in gastric juice, which is very conducive to the absorption of drugs in the body. Any ratio mangiferin-berberine composition can not increase the solubility in the acidic water.

DETAILED DESCRIPTION OF TECHNOLOGY SCHEMES

The present invention provides a mangiferin-berberine salt that has the following characteristics:

① In present invention, mangiferin-berberine salt has the general formula (I):

② The melting point of the mangiferin-berberine salt is 176° C.-178° C.

The mangiferin-berberine salt also has the following characteristics: the $^{13}$CNMR data of mangiferin-berberine salt has the following characteristics: The chemical shift of $C_6$, $C_{13a}$, $C_{8a}$, $C_{12a}$ of berberine change markedly owing to shielding effect.

The mangiferin-berberine salt also has the following characteristics: the $^{13}$CNMR data of mangiferin-berberine salt has the following characteristics: The chemical shift of $C_3$ and $C_7$ of mangiferin change markedly owing to low shielding effect.

The present invention provides a method for preparation of mangiferin-berberine salt:

① mangiferin is reacted with alkaline sodium (or potassium), to produce mangiferin monosodium (or monopotassium) salt;

② mangiferin monosodium (or monopotassium) salt is reacted with berberine, to produce mangiferin-berberine salt.

The method for preparation is as follows:

① Mangiferin is suspended in a solvent; the water solution of alkaline sodium (or potassium) is added into the suspension while mixing round until the solution is clear; then the reaction solution is filtrated to get solution A.

② Berberine is added into water to dissolve then filtrated to get solution B.

③ Solution A is dropped into solution B while B solution is being stirred; after the solution A is used up, the reaction solution is mixed continuously in order to react completely; a lot of deposition is produced. The reaction solution is filtrated to get the deposition. The solid substance is dried to get mangiferin-berberine salt.

In the method of preparation as defined above, the molecular ratio of mangiferin and alkaline sodium (or potassium) is 1:0.5-1.0.

In the method of preparation as defined above, the molecular ratio of mangiferin monosodium (or monopotassium) salt and berberine is 1:1.

In the method of preparation as defined above, the alkaline sodium (or potassium) is single salt or mixture, such as sodium carbonate, sodium bicarbonate, potassium carbonate, potassium bicarbonate, sodium acetate or potassium acetate etc.

In the method of preparation as defined above, the solvent is a mixture, which is water mixed with one or more than two kinds of organic solvent, such as ethanol or methanol or acetone, which can dissolve in water at discretion. The ratio of water is 10-90% (v/v).

In the method of preparation as defined above, berberine can also be berberine hydrochloride, berberine sulfate, tannin berberine or other medically acceptable salt of berberine. The preferred compound is berberine, berberine hydrochloride, and berberine sulfate.

Physical and chemical properties of mangiferin-berberine salt:

Orange powder, melting point: 176-178° C., Almost insoluble in water, slightly soluble in boiling water. Its chemical structure is as follows:

Identification of mangiferin-berberine salt:

The $^{13}$CNMR (400 MHz) data of mangiferin-berberine salt, mangiferin and berberine are as follows:

| Carbon number | $^{13}$CNMR(DMSO-$d_6$) ($\delta$ppm) | $^{13}$CNMR(DMSO-$d_6$) ($\delta$ppm) mangiferin-berberine salt | Chemical shift effects ($\delta$ppm) |
|---|---|---|---|
| | mangiferin | | |
| C4 | 94.24 | 93.8 | −0.44 |
| C4b | 102.21 | 100.29 | −1.92 |
| C5 | 103.56 | 101 | −2.56 |
| C2 | 108.49 | 106.15 | −2.34 |
| C8 | 108.98 | 102.86 | −6.12 |
| C8a | 112.64 | 107.72 | −4.92 |
| C7 | 144.62 | 147.36 | +3.71 |
| C8b | 151.69 | 147.56 | −4.13 |
| C6 | 154.91 | 154.51 | −0.4 |
| C4a | 157.14 | 156.53 | −0.61 |
| C1 | 162.7 | 162.45 | −0.25 |
| C3 | 164.74 | 166.23 | +1.49 |
| C9 | 180.0 | 177.91 | −2.09 |
| C6' | 62.41 | 61.86 | −0.55 |
| C4' | 71.14 | 71.16 | +0.02 |
| C2' | 71.55 | 71.7 | +0.15 |
| C1' | 73.99 | 74.21 | +0.22 |
| C3' | 79.89 | 80.16 | +0.27 |
| C5' | 82.49 | 82.32 | −0.17 |
| | berberine | | |
| C5 | 28.24 | 27.14 | −1.1 |
| C6 | 57.20 | 55.87 | −1.33 |
| C10(—OCH$_3$) | 57.61 | 57.64 | +0.03 |
| C9(—OCH$_3$) | 62.56 | 62.56 | 0 |
| —O—CH$_2$—O | 103.68 | 102.69 | −0.99 |
| C1 | 106.54 | 105.73 | −0.81 |
| C4 | 109.40 | 109.01 | −0.39 |
| C1a | 121.49 | 120.89 | −0.6 |
| C13 | 121.86 | 121.07 | −0.79 |
| C8a | 123.33 | 121.97 | −1.36 |
| C12 | 124.55 | 124.18 | −0.37 |
| C11 | 128.04 | 126.99 | −1.05 |
| C4a | 131.90 | 131.15 | −0.75 |
| C12a | 135.13 | 133.56 | −1.57 |
| C13a | 139.65 | 137.96 | −1.69 |
| C8 | 145.73 | 145.69 | −0.04 |
| C9 | 146.42 | 144.12 | −2.3 |
| C2 | 149.92 | 149.79 | −1.59 |
| C10 | 152.02 | 150.48 | −1.54 |
| C3 | 152.17 | 150.89 | −1.28 |

The $^1$HNMR (400 MHz) data of mangiferin-berberine salt, mangiferin and berberine are as follows:

| Hydrogen number | $^1$HNMR(DMSO-$d_6$) ($\delta$ppm) | $^1$HNMR(DMSO-$d_6$) ($\delta$ppm) mangiferin-berberin salt | Chemical shift effects ($\delta$ppm) |
|---|---|---|---|
| | mangiferin | | |
| H1' | 4.60 | 4.56 | −0.04 |
| H5 | 6.37 | 6.01 | −0.36 |
| H4 | 6.86 | 6.15 | −0.71 |
| H8 | 7.39 | 6.88 | −0.51 |
| | berberine | | |
| H1 | 7.8 | 7.75 | −0.05 |
| H4 | 7.09 | 7.05 | −0.04 |
| H5 | 3.19 | 3.11 | −0.08 |
| H6 | 4.92 | 4.90 | −0.02 |
| H8 | 9.9 | 9.84 | −0.06 |
| H9 (OCH3) | 4.11 | 4.05 | −0.06 |
| H10 (OCH3) | 4.21 | 4.08 | −0.13 |
| H11 | 8.19 | 8.14 | −0.05 |
| H12 | 7.99 | 7.92 | −0.07 |

-continued

| Hydrogen number | $^1$HNMR(DMSO-$d_6$) (δppm) | $^1$HNMR(DMSO-$d_6$) (δppm) mangiferin-berberin salt | Chemical shift effects (δppm) |
|---|---|---|---|
| H13 | 8.96 | 8.86 | −0.1 |
| H(O—CH2—O) | 6.17 | 6.16 | −0.01 |

Analysis of the above structural identification data is as below:

The $^{13}$CNMR (400 MHz) data of mangiferin-berberine salt are compared with that of mangiferin and berberine: The chemical shift of $C_6$, $C_{13a}$, $C_{8a}$, $C_{12a}$ and other carbon of berberine change markedly owing to shielding effect, and the chemical shifts of other carbon atoms of berberine also change varying degrees. The chemical shifts of $C_3$ and $C_7$ of mangiferin change markedly owing to low shielding effect, and the chemical shifts of other carbon atoms of mangiferin also change varying degrees owing to shielding effect.

The $^1$HNMR (400 MHz) data of mangiferin-berberine salt are compared with that of mangiferin and berberine:

The chemical shift of $H_5$, $H_{12}$, $H_{13}$ and other hydrogen atoms of berberine change markedly owing to shielding effect, the chemical shift of other carbon atoms of berberine also change varying degrees. The chemical shift of the end proton $H_1$', three phenyl proton $H_4$, $H_5$, $H_8$ and other hydrogen atoms of mangiferin change markedly owing to shielding effect.

The chemical shift changes in NMR data show that: the chemical environment of the atom has changed in the mangiferin group and berberine group, indicating that berberine group and mangiferin group combine to form a mangiferin-berberine salt.

Mangiferin-berberine salt may be prepared in clinically acceptable formulations with pharmaceutical acceptable auxiliary material. The formulations may be oral formulations or external formulations and injection formulations etc., such as a tablet, a capsule, a gentle capsule, a granule, a pill, a syrup, an oral solution, an oral suspension, gel, freeze-dried power and the like.

The present invention also provides that mangiferin-berberine salt is used as AMPK activator.

The present invention also provides the drug that mangiferin-berberine salt is active ingredient is used as AMPK activator.

According to the revealing that AMPK plays an important role in the development of disease in modern medicine, AMPK activator can be used to prevent or treat one or more of such diseases: Diabetes, a variety of chronic diabetes complications (including coronary heart disease, atherosclerosis, cerebrovascular disease and other major vascular disease; diabetic nephropathy, diabetic retinopathy and other microvascular disease; neuropathy; diabetic foot; diabetic maculopathy, cataracts, glaucoma, refractive changes, such as iris and ciliary body disease and other eye diseases, etc.), obesity, hyperlipidemia, insulin resistance, hyperinsulinemia, X syndrome, myocardial hypertrophy, arrhythmia, atherosclerosis, ischemic heart disease, heart failure, hypertension, upper respiratory tract infection, chronic bronchitis, chronic obstructive pulmonary disease, asthma, pulmonary fibrosis, hepatitis, fatty liver, alcoholic liver, liver fibrosis, cirrhosis, prostatitis, pancreatitis, nephritis, nephrotic syndrome, chronic renal failure, rheumatoid arthritis, rheumatoid arthritis, osteoarthritis, inflammatory bowel disease, Alzheimer's disease, memory impairment, infarct dementia, Parkinson's disease, tumors (including tumor radiotherapy, chemotherapy is not sensitive; cancer radiotherapy, chemotherapy toxicity generated), muscle atrophy, muscle weakness disease.

The present invention provides that mangiferin-berberine salt is used as AMPK activator. The AMPK activator can also be used as sport substitute.

The present invention provides that the effective dose range of mangiferin-berberine salt is 0.1-30 mg/kg/day for the every person when mangiferin-berberine salt is used as AMPK activator. The dose as above is based on the results that are obtained in vitro and in animal experiments. Because of the difference between animals and the human body, between diseases, between in vitro and in vivo, so the adjustments of the actual clinical application dose can be allowed. Usage can be selected according to the specific disease, oral is preferred.

Embodiments of the invention may be explained in detail in the following examples given below. These examples are provided as further illustration of the invention, and therefore should not be construed to limit the scope of the invention.

DETAILED EMBODIMENTS

The mangiferin in the invention can be purchased from market (Guangxi Baise Tianxing Technology Development Co., Ltd., the factory which has the corresponding equipment can produce). The berberine hydrochloride and berberine and so on in the invention can be purchased from market (Xi'an Xiaocao Plant Technology Co., Ltd.). The reagent in present invention like sodium carbonate, sodium bicarbonate, potassium carbonate, potassium bicarbonate etc. can be purchased from market.

Embodiment 1

Preparation of Mangiferin-Berberine Salt

Mangiferin 42.2 g (0.1 mol) is suspended in the mixture of water 1800 ml and ethanol 600 ml in reactor, mixing round adequately. Sodium bicarbonate 8.4 g (0.1 mol) is dissolved in water, the concentration is 0.5% (w/v). The solution of sodium bicarbonate is added slowly into the suspended mangiferin solution while mixing round until the solution is clear, then the reaction solution is filtrated to get solution A. Berberine 33.6 g (0.1 mol) is added into boiling water 1500 ml to dissolve then filtrated to get solution B. Solution A is added slowly into solution B, mixing around adequately, and then put for 12 hours; a lot of deposition is produced. The reaction solution is filtrated to get the deposition. The deposition is washed fully with water, The solid substance is dried in vacuum below 60° C. to get brown mangiferin-berberine salt 53.4 g. The productivity is 70.5%. The purity of mangiferin-berberine salt is 98.6% as detected by HPLC.

Embodiment 2

Preparation of Mangiferin-Berberine Salt

Mangiferin 42.2 g (0.1 mol) is suspended in the mixture of water 2000 ml and ethanol 800 ml in reactor, mixing round adequately. Sodium carbonate 5.3 g (0.05 mol) is dissolved in water, the concentration is 1% (w/v). The solution of sodium carbonate is added slowly into the suspended mangiferin solution while mixing round until the solution is clear, then the reaction solution is filtrated to get solution A. Berberine hydrochloride 37.3 g (0.1 mol) is added into boiling water 2500 ml to dissolve then filtrated to get solution B. solution A is added slowly into solution B, mixing round adequately, and then put for 12 hours; a lot of deposition is produced. The reaction solution is filtrated to get the deposition. The deposition is washed fully with water, The solid substance is dried in vacuum below 60° C. to get brown mangiferin-berberine salt 53.3 g. The productivity is 67.4%. The purity of mangiferin-berberine salt is 98.5% as detected by HPLC.

Embodiment 3

Preparation of Mangiferin-Berberine Salt

Mangiferin 42.2 g (0.1 mol) is suspended in the mixture of water 1600 ml and methanol 800 ml in reactor, mixing round adequately. Potassium carbonate 6.9 g (0.05 mol) is dissolved in water, the concentration is 0.2% (w/v). The solution of potassium carbonate is added slowly into the suspended mangiferin solution while mixing round until the solution is clear, then the reaction solution is filtrated to get solution A. Berberine sulfate 43.2 g (0.1 mol) is added into boiling water 2500 ml to dissolve then filtrated to get solution B. Solution A is added slowly into solution B, mixing round adequately, and then put for 12 hours; a lot of deposition is produced. The reaction solution is filtrated to get the deposition. The deposition is washed fully with water, The solid substance is dried in vacuum below 60° C. to get brown mangiferin-berberine salt 51.8 g. The productivity is 60.6%. The purity of mangiferin-berberine salt is 98.6% as detected by HPLC.

Embodiment 4

Preparation of Mangiferin-Berberine Salt

Mangiferin 42.2 g (0.1 mol) is suspended in the mixture of water 1000 ml and methanol 1000 ml in reactor, mixing round adequately. Potassium bicarbonate 10.0 g (0.1 mol) is dissolved in water, the concentration is 2% (w/v). The solution of potassium bicarbonate is added slowly into the suspended mangiferin solution while mixing round until the solution is clear, then the reaction solution is filtrated to get solution A. Berberine 33.6 g (0.1 mol) is added into boiling water 2500 ml to dissolve then filtrated to get solution B. Solution A is added slowly into solution B, mixing around adequately, and then put for 12 hours; a lot of deposition is produced. The reaction solution is filtrated to get the deposition. The deposition is washed fully with water, The solid substance is dried in vacuum below 60° C. to get brown mangiferin-berberine salt 49.5 g. The productivity is 65.3%. The purity of mangiferin-berberine salt is 98.5% as detected by HPLC.

Embodiment 5

Preparation of Mangiferin-Berberine Salt

Mangiferin 42.2 g (0.1 mol) is suspended in the mixture of water 3000 ml and acetone 300 ml in reactor, mixing round adequately. Sodium carbonate 5.3 g (0.05 mol) is dissolved in water; the concentration is 5% (w/v). The solution of sodium carbonate is added slowly into the suspended mangiferin solution while mixing round until the solution is clear, then the reaction solution is filtrated to get solution A. Berberine 33.6 g (0.1 mol) is added into boiling water 2500 ml to dissolve then filtrated to get solution B. Solution A is added slowly into solution B, mixing around adequately, and then put for 12 hours; a lot of deposition is produced. The reaction solution is filtrated to get the deposition. The deposition is washed fully with water, The solid substance is dried in vacuum below 60° C. to get brown mangiferin-berberine salt 50.9 g. The productivity is 67.2%. The purity of mangiferin-berberine salt is 98.5% as detected by HPLC.

Embodiment 6

Preparation of Mangiferin-Berberine Salt

Mangiferin 42.2 g (0.1 mol) is suspended in the mixture of water 300 ml and ethanol 3000 ml in reactor, mixing round adequately. Sodium carbonate 5.3 g (0.05 mol) is dissolved in water; the concentration is 0.2% (w/v). The solution of sodium carbonate is added slowly into the suspended mangiferin solution while mixing round until the solution is clear, then the reaction solution is filtrated to get solution A. Berberine 33.6 g (0.1 mol) is added into boiling water 3000 ml to dissolve then filtrated to get solution B. Solution A is added slowly into solution B, mixing around adequately, and then put for 12 hours; a lot of deposition is produced. The reaction solution is filtrated to get the deposition. The deposition is washed fully with water, The solid substance is dried in vacuum below 60° C. to get brown mangiferin-berberine salt 51.6 g. The productivity is 68.1%. The purity of mangiferin-berberine salt is 98.6% as detected by HPLC.

Embodiment 7

Preparation of Mangiferin-Berberine Salt Tablets

The formulation is as follows:
mangiferin-berberine salt 333 g microcrystalline cellulose 200 g starch 300 g
The total is 10000 tablets.
Mangiferin-berberine salt that is obtained by the method of embodiments as above is smashed and through 100 mesh sieve, mangiferin-berberine salt and starch and microcrystalline cellulose are put into together mixing round uniformly. Appropriate bonding material is spray in the powder to make soft material, which is formed into granules. The granules are dried and then tablets are pressed by a tablet pressing machine. 10000 tablets are prepared. There is 33.3 mg mangiferin-berberine salt in every tablet.

Embodiment 8

Preparation of Mangiferin-Berberine Salt Granule

The formulation is as follows:
mangiferin-berberine salt 10 g carboxymethyl cellulose 490 g xylose 500 g
The total is 1000 g.
Mangiferin-berberine salt that is obtained by the method of embodiments as above is smashed and through 100 mesh sieve, mangiferin-berberine salt and carboxymethyl cellulose and xylose are put in together mixing round uniformly. Appropriate bonding material is sprayed in the powder to make soft material, which is formed into granules. The granules are dried. 1000 g granule is prepared. There is 10 mg mangiferin-berberine salt in every gram.

Embodiment 9

Preparation of Mangiferin-Berberine Salt Capsules

The formulation is as follows:
Mangiferin-berberine salt 333 g microcrystalline cellulose 100 g starch 600 g
Mangiferin-berberine salt that is obtained by the method of examples as above is smashed and through 100 mesh sieve, mangiferin-berberine salt and microcrystalline cellulose and starch are put in together mixing round uniformly. Appropriate bonding material is sprayed in the powder to make soft material, which is formed into granules. The granules are dried and then put into capsules. There is 33.3 mg mangiferin-berberine salt in every capsule.

Embodiment 10

Preparation of Mangiferin-Berberine Salt Suspension

Mangiferin-berberine salt 10 g that is obtained by the method of embodiment as above is smashed into superfine powder, carboxymethylcellulose sodium and ethylparoben and water are made into mucilage, then mangiferin-berberine salt and syrupus simplex and put into with mixing round, then it is added water to 1000 ml, mixing uniformly. There is 10 mg mangiferin-berberine salt in every milliliter.

The Solubility of Mangiferin-Berberine Salt:

5 mg mangiferin-berberine salt powder which is weighed up accurately is put into 50 ml distilled water under 25° C.±2° C., the solution is shaken strongly 30 seconds every 5 minutes. There are solute particles in 30 minutes. The water solubility of mangiferin-berberine salt is less than 0.1 mg/ml. Mangiferin-berberine salt is hardly solubility substance in water.

The Solubility of Mangiferin-Berberine Salt in Different pH Water:

Take pure water; add hydrochloric acid to adjust pH to 1 and 3 and 5 separately. Take the water 50 ml of different pH; weigh up accurately 50 mg mangiferin-berberine salt powder, put into the 50 ml water as above, shake and observe dissolved phenomena. Mangiferin-berberine salt dissolved rapidly in the water of pH 1 in a few seconds, mangiferin-berberine salt dissolved in the water of pH 3 in five minutes, mangiferin-berberine salt did not dissolve completely in the water of pH 5.

Take the water 50 ml of different pH 1 and 3; weigh up accurately 100 mg mangiferin-berberine salt powder, put into the 50 ml water as above, shake and observed dissolved phenomena. Mangiferin-berberine salt dissolved in the water of pH 1 in a minute, mangiferin-berberine salt did not dissolve completely in the water of pH 3.

Take the water 50 ml of pH 1; weigh up accurately 200 mg mangiferin-berberine salt powder, put into the 50 ml water as above, shake and observed dissolved situation. Mangiferin-berberine salt can dissolve in the water of pH 1, but there is precipitation soon in the solution.

Take the water 50 ml of pH 1 for three copies; weigh up accurately 50 mg mangiferin and berberine composition powder (the molecular ratio of mangiferin and berberine is 1:1, 1:3, 1:5), put into the 50 ml water as above separately, shake and observed dissolved phenomena. The trace of the mangiferin and berberine compositions that include all ratios as above can dissolve.

Mark all above the mangiferin-berberine salt solutions, places them at room temperature, observe the phenomenon within 24 hours. In the solution of pH 1 and 3, trace precipitate is found in the solutions that concentration is 1 mg/ml and 2 mg/ml in 12 hours; in the solution of pH 1, there is more precipitate in the solutions that concentration is 4 mg/ml in 12 hours.

Stability of Mangiferin-Berberine Salt

Put several parts of mangiferin-berberine salt into glass bottles, seal, set inside drug stability chamber, set accelerated testing conditions to: 40° C.±2° C./75% RH+5% RH. At 0 and 1 and 2 months, sample, determine the content of mangiferin-berberine salt by HPLC. The results showed that the content of mangiferin-berberine salt do not significantly change in accelerated test conditions, suggesting that the shelf time of mangiferin-berberine salt at room temperature is longer than 1 year.

To illustrate the pharmacological activity of mangiferin-berberine salt in the summary of the invention described, the inventors include both in vitro and in vivo experimental studies; the inventors use one typical disease model to represent a class of diseases. They studies the effects of mangiferin-berberine salt on the phosphorylation of AMPK and chemosensitizing on tumor cells in vitro; they use KK-ay mice to represent the glucose and lipid metabolism disorders and use rheumatoid arthritis rats to represent autoimmune diseases and use Alzheimer's disease rats to represent neurodegenerative diseases separately, in order to illustrate the feasibility that mangiferin-berberine salt treats various diseases as AMPK activator. Elaborated as follows:

The activation of mangiferin-berberine salt on AMPK

1. Materials

Mangiferin-berberine salt that is obtained by the method of embodiments as above dissolves in DMSO. Before use it is diluted by culture medium or HBS. The ultimate concentration of DMSO is less than 0.2%.

The rat L6 cell line was obtained from the ATCC. HG-DMEM was from GIBCO™. Fetal bovine serum (FBS) was purchased from Hyclone. Anti-AMPK, anti-ACC, antiphospho-AMPK (Thr172), antiphospho-ACC (ser79) polyclonal antibodies were from Cell Signal Technology.

2. Method 2.1 Cell culture

L6 cells were grown in HG-DMEM containing 10% (v/v) FBS, 100 units/ml penicillin and 100 U/ml streptomycin in a humidified atmosphere of 5% CO2 at 37° C. When the cells covered 60%, the medium was switched to HG-DMEM with 2% FBS and the culture medium was replaced every two days until that the cells covered about 90%.

2.2 The Treatment and Collection of Samples

Cells in 6-well plates were starved in serum-free HG-DMEM, and then samples were added into serum-free HG-DMEM; the concentration of DMSO is 0.2%. The samples incubated for 3 h in the cells. Cells were rinsed twice with ice-cold 1×PBS and lysed with 200 μl 1×SDS loading buffer (50 mM Tris.HCL, 100 mM DTT, 2% SDS, 0.1% bromophenol blue, 10% glycerol). Collected lysis buffer, ultrasound for 15 seconds, boiled at 100° C. for 10 minutes.

2.3 Western Blot

Samples were electrophoresed on 10% SDS-polyacrylamide gels, and transferred to PVDF membranes under 100V and 1-2 h in the transmembrane instrument. Protein in the gel was transferred to nitrocellulose membrane under the state of half dry, and the band was determined by Ponceau S (Ponceau S). The membrane was closed in blocking solution (3% non-fat dry milk, 0.1% Tween, TBS solution) for 1 hour; primary antibodies were added at 1:1000 at 4° C. overnight, washed by TBS for 3×15 min; the secondary antibodies were added at 1:1000, incubated for 1 hour at room temperature, washed by TBS for 3×15 min, placed on the ECL and washed for 5-10 min, and imaged by X-ray.

3. Results

Mangiferin-berberine salt (1.25-5 μmol/L) increases significantly the phosphorylation of both AMPK and ACC in dose-dependent manner.

The Chemosensitizing Effects of Mangiferin-Berberine Salt on Tumor Cells

1. Materials

Mangiferin-berberine salt (BM) was obtained by the method of embodiments as above. Cisplatin (DDP), adriamycin (ADM) and taxol were purchased from the market. Samples were dissolved in DMSO.

2. Groups

DMSO group, BM group (20 μmol/L), DDP group (1 μmol/L), ADM group (1 μmol/L), TAXOL group (1 μmol/L), BM (20 μmol/L)+DDP (1 μmol/L) group, BM (20 μmol/L)+ADM (1 μmol/L) group, BM (20 μmol/L)+TAXOL (1 μmol/L) group.

3. Method

In accordance with $10^3$-$10^4$/well, cultured human hepatoma cell line Bel-7402 200 μl per well were inoculated into 96-well cell culture plate, the samples were added after 24 hours. For those groups which are composed of two samples, after mangiferin-berberine salt and cells were cultured together for 3 h, DDP or ADM or TAXOL were added, cultured for 72 h. Finally cell toxicity was determined by tetrazolium salt reduction (MTT). Experiments were repeated twice.

4. Results

Figure 1:
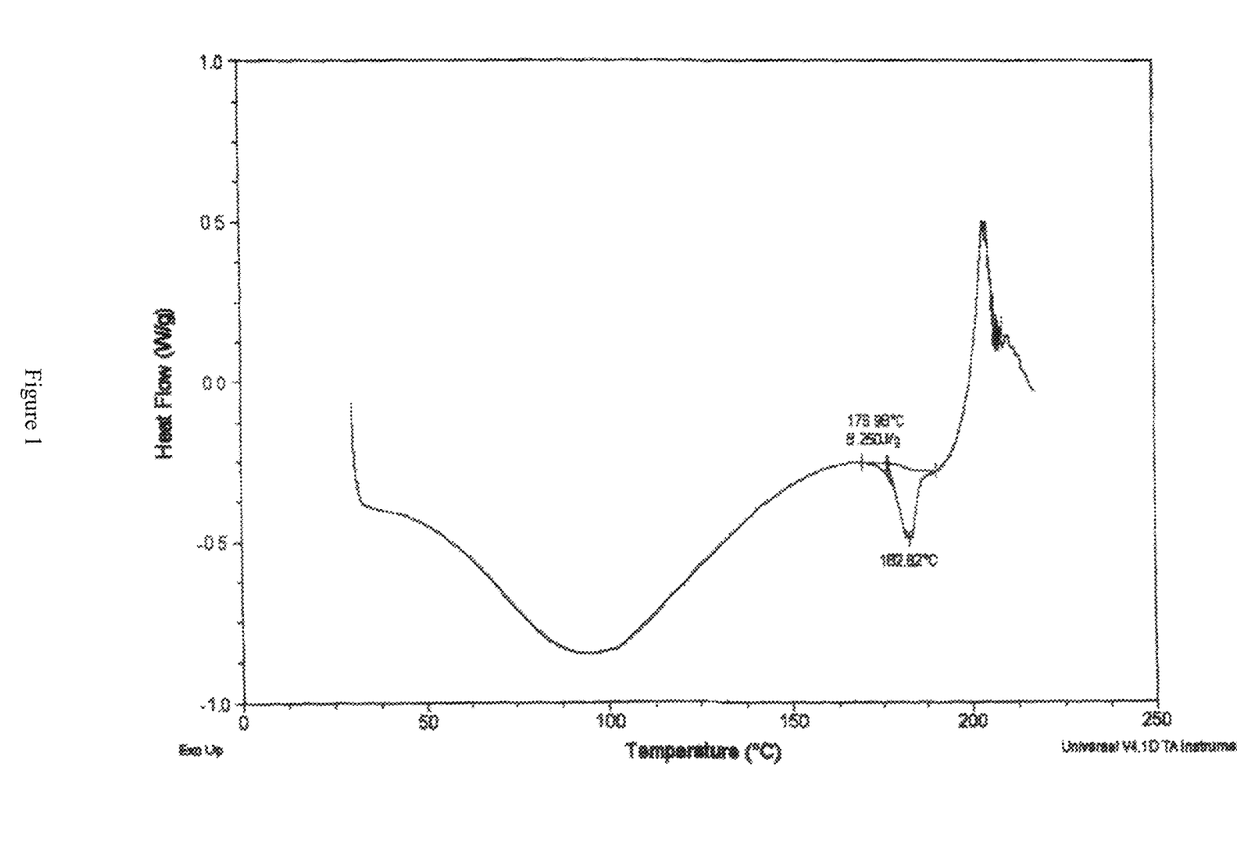
FIG. 1 illustrates the differential scanning calorimetry (DSC) curve of mangiferin-berberine salt.
Figure 2:
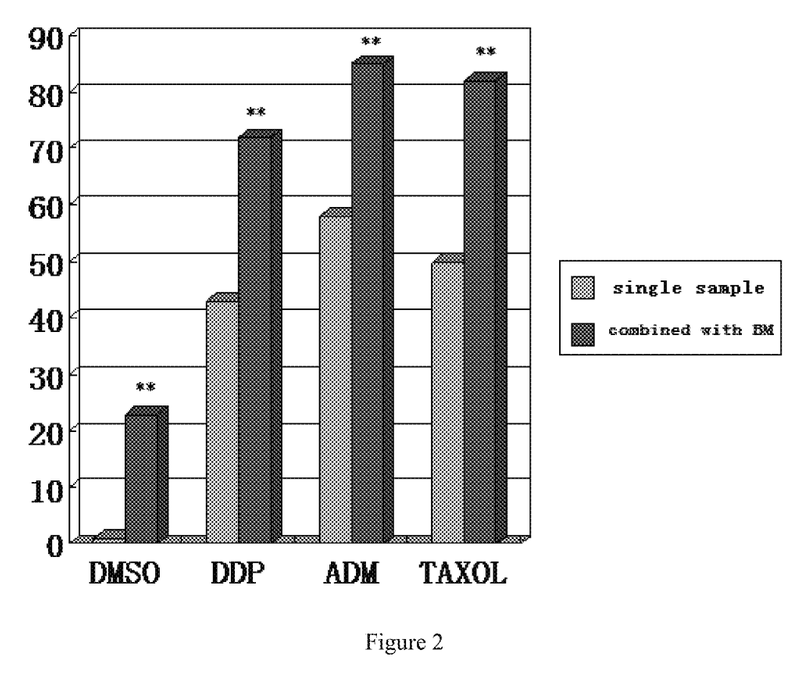
FIG. 2 illustrates the effect of mangiferin-berberine salt on tumor cytotoxicity. The vertical axis is cell death (%). (Note: compared with single sample group: *P>0.05, **P>0.01)

The cytotoxicity of mangiferin-berberine salt combined with DDP or ADM or TAXOL group was significantly higher than the cytotoxicity of DDP or ADM or TAXOL alone. Mangiferin-berberine salt can increase the cytotoxic effect of chemotherapy (FIG. 2).

The Effect of Mangiferin-Berberine Salt on KK-ay Mice

1. Materials

Mangiferin-berberine salt was obtained by the method of examples as above. Mangiferin-berberine salt was suspended with 3‰ sodium carboxymethyl cellulose before use. Rosiglitazone hydrochloride was purchased from Zhejiang wanma pharmaceutical Co., Ltd.

2. Animals

KK-ay mice, 16 weeks age, male.

3. Experimental Group:

KK-ay mice group (n=10); mangiferin-berberine salt low dose group (20 mg/kg, n=10, BML); mangiferin-berberine salt middle dose group (40 mg/kg, n=10, BMM); mangiferin-berberine salt high dose group (80 mg/kg, n=10), BMH metformin group[500 mg/kg, n=10]. Test samples or vehicle control was given orally for 30 days. KK-ay mice group were given vehicle.

4. Measurements:

The blood specimens were taken at the end of the experiment. Plasma glucose (GLU, mmol/L), lipid [triglycerides (TG, mmol/L), total cholesterol (TC, mmol/L), low density lipoprotein (LDL, mmol/L), high density lipoprotein (HDL, mmol/L)], liver enzyme [ALT(U/L) and AST(U/L)] were determined using GF-D800 semi-auto chemist which was purchased from Shandong Gaomi Caihong Analytical Instrument Co., Ltd.

Insulin: Radioimmunoassays (RIA), γ counter counts. insulin RIA Kit was purchased from Shandong Weifang City three-dimensional (3V) Biological Company. Urinary albumin. Collected urine for 24 h by metabolic cages, and recorded the output of urine. Urine was centrifuged, supernatant was taken, it was saved at −80° C. Free urinary were collected weekly Monday 13:00 by tail raise reflection. Assay urinary albumin by competitive ELISA, calculate the urinary albumin excretion rate (urinary albumin excretion rate=urinary albumin concentration (mg/L)×urine volume (ml)/total collection time (minutes)=mg/min, UAER), the units of figure is mg/24 h.

5. Statistics:

The results have been calculated as mean±SD ($\bar{x}$±SD) and comparisons of the data have been done by t-test.

Figure 3:
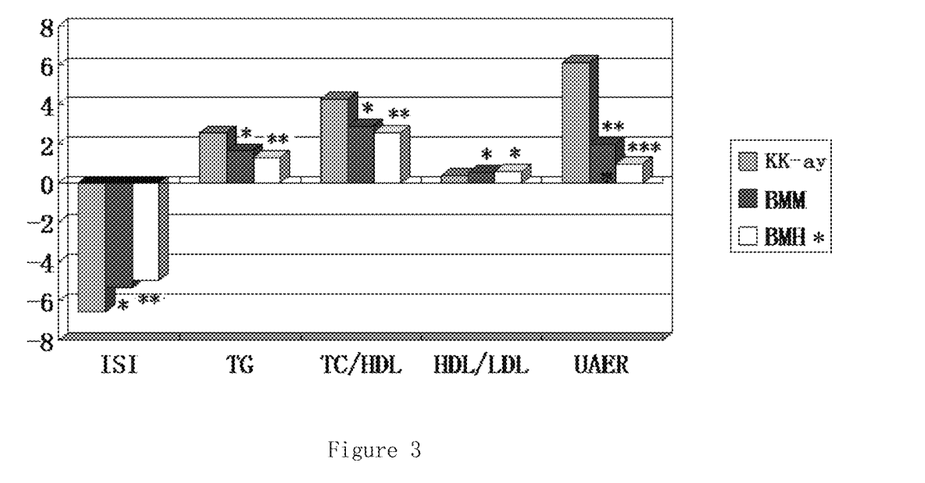
FIG. 3 illustrates the effect of mangiferin-berberine salt on ISI and lipid in KK-ay mice. (Note: compared with model group: *P>0.05, P>0.01, *P>0.001)
Figure 4:
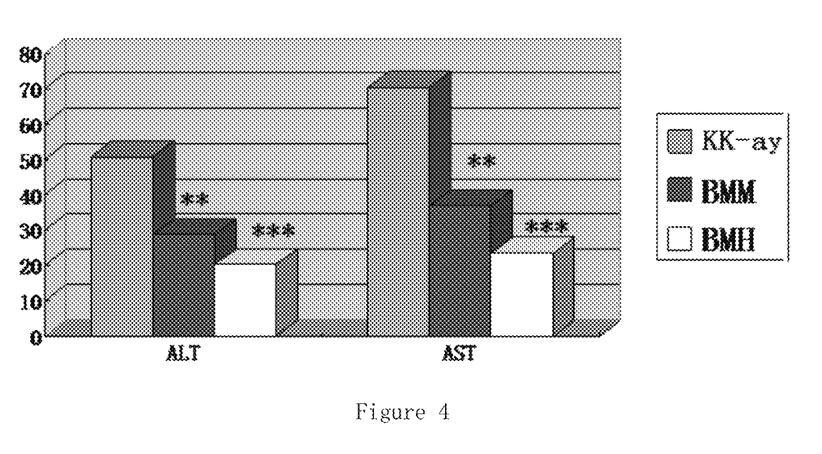
FIG. 4 illustrates the effect of mangiferin-berberine salt on liver enzymes in KK-ay mice. (Note: compared with model group: *P>0.05, **P>0.01)

6. Results 40 mg/kg mangiferin-berberine salt can significantly improves blood glucose, lipid, INS, UAER, ISI and liver enzymes in KK-ay mice (FIG. 3-4).

The Effect of Mangiferin-Berberine Salt on Dementia Rats

1. Materials

1.1 Animals

SD male rats, SPF, 250~300 g, free drinking water and eating food, before the experiment in a lab environment adapted for 2-3d, the temperature of the laboratory was controlled at 25° C., relative humidity was 40%-80%.

1.2 Samples, Reagents and Equipment:

Mangiferin-berberine salt was obtained by the method of examples as above.

Condensed β-amyloid peptide fragment 1 to 40 ($A_{\beta1-40}$) was purchased from Sigma, USA.

Experimental animals the stereotaxic instrument (SN2 type) was purchased from Japan ChengMao Company.

Water maze was purchased from Chinese Academy of Medical Sciences.

3. Experimental Group:

Sham surgery rats group (control group, n=10) were injected the saline of an equal volume in the hippocampus; model rats group (n=10) were treated by $A_{\beta1-40}$; mangiferin-berberine salt low dose group (20 mg/kg, n=10, BML); mangiferin-berberine salt middle dose group (40 mg/kg, n=10, BMM); mangiferin-berberine salt high dose group (80 mg/kg, n=10, BMH).

Test samples or vehicle control was given orally for 4 weeks, one week before modeled. Maze training period, administrated in 0.5 h before training.

3. Method

3.1 The Preparation of the Model that AD was Induced by $A_{\beta1-40}$:

Injected 440 into the hippocampus of rats to establish animal model of AD. As follows:

SD rats were injected $A_{\beta1-40}$ 1 μl each side into the bilateral hippocampus under the experimental animals the stereotaxic instrument ($A_{\beta1-40}$ was dissolved in sterile saline 10 μg/μl, incubated at 37° C. for one week before use.) Injection site: 3.5 mm after the bregma, 2.0 mm beside midline brain, and the depth of is 2.7 mm.

3.2 Measurements

Spatial learning and memory tests: Morris water maze method. Platform located in the northeast quadrant of the middle of the maze; the water level is 1.5 cm above the platform; the temperature of water was maintained at 19° C.~20° C.; rats were continuously training for 5d, twice a day; we set the maximum swimming time of 70s, recorded the time that rats found the platform (latent period, EL) by stopwatch.

Figure 5:
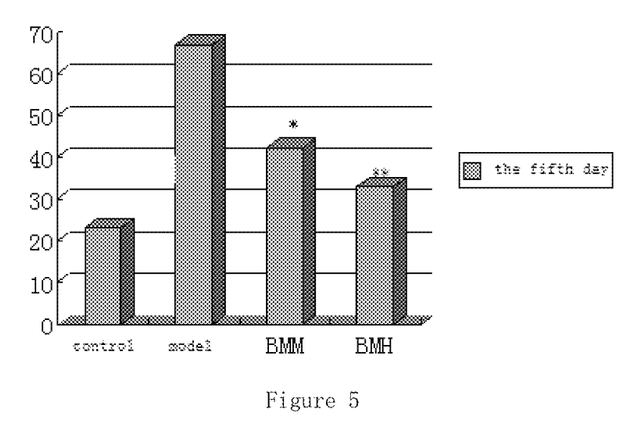
FIG. 5 illustrates the effect of mangiferin-berberine salt on learning and memory in dementia rats. (Note: compared with model group: *P>0.05, **P>0.01)

4. Results:

Increasing the days of training, the average EL of the rats was gradually reduced. Compared with the EL of the sham surgery group, the EL of model group was significantly longer, significantly different in fourth day, indicated the model succeed. The EL of fifth day for every group was compared. The results showed that the EL of mangiferin-berberine salt of the high and middle dose were significantly reduced. It shows that mangiferin-berberine salt can significantly improve the $A_{\beta1-40}$-induced space learning and memory impairment (FIG. 5).

The Effect of Mangiferin-Berberine Salt on Rheumatoid Arthritis Rat

1. Materials

Wistar rats, female, 100±20 g. Acid-soluble Bovine-derived collagen type II (Collagen II) and Freund's incomplete adjuvant was purchased from Sigma. TNF-α kit was purchased from Nanjing Jiancheng Biological Engineering Institute.

2. Model

The Acid-soluble Bovine-derived collagen type II (C II) with Freund's incomplete adjuvant, was made up to 2.5 mg/ml emulsion, Every rat was injected emulsion containing 250 μg/100 μC II by intradermal in the right rear paw in order to inflame.

Control group: Every rat was injected the emulsion 100 μl that was not comprised C II and only comprised Freund's incomplete adjuvant.

3. Experimental Group:

Normal rats group (control group, n=10); model rats group (n=10); mangiferin-berberine salt low dose group (10 mg/kg, n=10, BML); mangiferin-berberine salt middle dose group (20 mg/kg, n=10, BMM); mangiferin-berberine salt high dose group (40 mg/kg, n=10, BMH); Dexamethasone Sodium Phosphate group (0.1 mg/kg, Dexa, n=10).

Two weeks after primary immunization, test samples or vehicle control was given orally for 4 weeks. Normal and model rats group were given the saline of an equal volume.

4. Measurements:

Foot swelling: Measurement the volume of right hind foot by capillary enlarge measure method, calculated swelling growth percentage [(value after administration−value before administration)/value before administration]×100%.

4.2 Cytokines: The blood specimens were taken from femoral artery at the end of the experiment, and serum was extracted, then frozen. TNF-α was measured according to the instructions of ELISA kit.

5. Results

Figure 6:
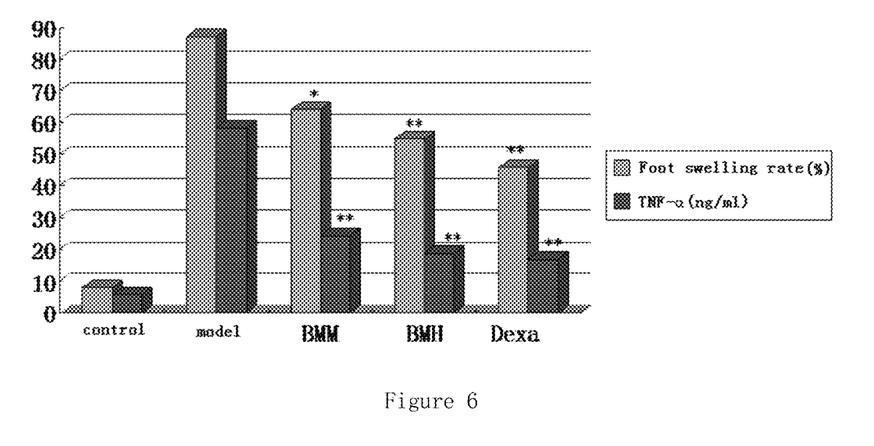
FIG. 6 illustrates the effect of mangiferin-berberine salt on rheumatoid arthritis rat (Note: compared with model group: *P>0.05, **P>0.01)

Mangiferin-berberine salt of high dose and middle dose significantly inhibited paw swelling and the secretion of cytokine TNF-α. It shows that mangiferin-berberine salt can treat rheumatoid arthritis in model rats (FIG. 6).

We claim:

1. Mangiferin-berberine salt having the following characteristics:

① the mangiferin-berberine salt has the general formula (I):

② the melting point of the mangiferin-berberine salt is 176° C.-178° C.

2. A drug, wherein the drug comprises an effective amount of the mangiferin-berberine salt as claimed in claim 1, and a pharmaceutically acceptable auxiliary material.

3. The drug according to claim 2, wherein the drug is any formulation in the form of a tablet, a capsule, a gentle capsule, a granule, a pill, a syrup, an oral solution, an oral suspension, gel, and freeze-dried power.

4. An AMPK activator, comprising the mangiferin-berberine salt of claim 1.

5. A method of preparation of the mangiferin-berberine salt according to claim 1, wherein:

① mangiferin is reacted with alkaline sodium or alkaline potassium, to produce mangiferin monosodium or mangiferin monopotassium) salt; and ② mangiferin monosodium or mangiferin monopotassium salt is reacted with be one of berberine, berberine hydrochloride, berberine sulfate, tannin berberine or other medically acceptable salt of berberine, to produce mangiferin-berberine salt.

6. The method of claim 4, wherein:

the molecular ratio of mangiferin and alkaline sodium or alkaline potassium is 1:0.5-1.0; and the molecular ratio of mangiferin monosodium or mangiferin monopotassium and the one of the berberine, the berberine hydrochloride, the berberine sulfate, the tannin berberine or other medically acceptable salt of berberine is 1:1.

7. The method of claim 5, wherein: the alkaline sodium or alkaline potassium is single salt or mixture consisting of sodium carbonate, sodium bicarbonate, potassium carbonate, potassium bicarbonate, sodium acetate, and potassium acetate.

8. The method of claim 5, wherein: the mangiferin monosodium or the mangiferin monopotassium salt is preferably reacted with one of berberine, berberine hydrochloride, berberine sulfate.

* * * * *

UNITED STATES PATENT AND TRADEMARK OFFICE
CERTIFICATE OF CORRECTION

PATENT NO.        : 8,673,864 B2
APPLICATION NO.   : 13/377863
DATED             : March 18, 2014
INVENTOR(S)       : Houlei Teng et al.

It is certified that error appears in the above-identified patent and that said Letters Patent is hereby corrected as shown below:

In the Claims

Claim 5, Column 16, line 42: "…salt is reacted with be one of berberine,…" should read - …salt is reacted with one of berberine,… -.

Claim 6, Column 16, line 46: "6. The method of claim 4, wherein:" should read - 6. The method of claim 5, wherein: -.

Signed and Sealed this
Second Day of September, 2014

Michelle K. Lee
*Deputy Director of the United States Patent and Trademark Office*